(12) United States Patent
Göpfert et al.

(10) Patent No.: US 11,480,534 B2
(45) Date of Patent: Oct. 25, 2022

(54) CALORIMETER AND SAMPLE CONTAINER FOR A CALORIMETER

(71) Applicant: Calbact AG, Kaiseraugst (CH)

(72) Inventors: Beat Göpfert, Frenkendorf (CH); Vinzenz von Tscharner, Rheinfelden (CH)

(73) Assignee: CALBACT AG, Kaiseraugst (CH)

( * ) Notice: Subject to any disclaimer, the term of this patent is extended or adjusted under 35 U.S.C. 154(b) by 399 days.

(21) Appl. No.: 16/757,374

(22) PCT Filed: Oct. 18, 2018

(86) PCT No.: PCT/EP2018/078475
§ 371 (c)(1),
(2) Date: Apr. 17, 2020

(87) PCT Pub. No.: WO2019/086251
PCT Pub. Date: May 9, 2019

(65) Prior Publication Data
US 2021/0190709 A1      Jun. 24, 2021

(30) Foreign Application Priority Data

Nov. 6, 2017   (EP) .................................... 17200227

(51) Int. Cl.
*G01N 25/00*  (2006.01)
*G01N 25/48*  (2006.01)
*B01L 3/00*   (2006.01)

(52) U.S. Cl.
CPC .......... *G01N 25/4826* (2013.01); *B01L 3/508* (2013.01); *B01L 2300/1805* (2013.01)

(58) Field of Classification Search
CPC .. B01L 3/505; B01L 3/508; B01L 7/00; B01L 2200/023; B01L 2300/042;
(Continued)

(56) References Cited

U.S. PATENT DOCUMENTS 3,210,996 A * 10/1965 Harwood .................. G01K 1/14
                                                            219/209
7,802,916 B2 * 9/2010 Teramoto ............... G01N 25/20
                                                            374/208
(Continued)

FOREIGN PATENT DOCUMENTS

AU    2018224292 A1 * 10/2019 .............. F24S 10/50
CN    102156148 A  *  8/2011 ......... G01N 25/4866
(Continued)

OTHER PUBLICATIONS

International Search Report of PCT/EP2018/078475, dated Nov. 2, 2018 (3 pages).

(Continued)

*Primary Examiner* — Gail Kaplan Verbitsky
(74) *Attorney, Agent, or Firm* — Hard IP LLC (57) ABSTRACT

A system comprising a calorimeter for measuring a heat flux of a sample comprising a recipient space for a sample container containing a sample, a heat sink, a first heat transducer whereby the first heat transducer comprises a heat receiving surface in contact with the sample container when the sample container is positioned in the recipient space and a heat absorbing surface in contact with the heat sink. A second heat sink is provided, whereby the second heat sink has a second heat receiving surface in contact with the heat (Continued)

sink and a second heat absorbing surface in contact with the sample container, when the sample container is positioned in the recipient space.

16 Claims, 7 Drawing Sheets

(58) Field of Classification Search
CPC ..... B01L 2300/0854; B01L 2300/0858; B01L 2300/123; B01L 2300/1805; B01L 2300/1822; G01K 17/00; G01N 25/20; G01N 25/4826; G01N 25/4853; G01N 25/486; G01N 33/487
USPC .......................... 374/29–40; 422/51; 436/141
See application file for complete search history.

(56) References Cited

U.S. PATENT DOCUMENTS

| | | | | |
|---|---|---|---|---|
| 7,947,223 B2 * | 5/2011 | Carlsson | ............. | G01K 17/006 422/68.1 |
| 9,593,988 B1 * | 3/2017 | Liberman | ............. | G01K 17/00 |
| 2004/0107986 A1 | 6/2004 | Nielson et al. | | |
| 2008/0304542 A1 * | 12/2008 | Danley | ............. | G01N 25/4833 374/31 |

FOREIGN PATENT DOCUMENTS

| | | | | | |
|---|---|---|---|---|---|
| EP | 0660110 | A1 | * | 6/1995 | |
| EP | 3106852 | A1 | * | 12/2016 | ............. G01K 17/00 |
| GB | 2093995 | A | | 9/1982 | |
| GB | 2547113 | A | * | 8/2017 | ............. G01N 25/20 |
| JP | 2009513974 | A | * | 4/2009 | |
| JP | 2019216074 | A | * | 12/2019 | |
| KR | 102328943 | B1 | * | 11/2021 | |
| RU | 2486497 | C1 | * | 6/2013 | |
| WO | WO-0208710 | A1 | * | 1/2002 | ........... G01K 17/006 |
| WO | 2007053105 | A1 | | 5/2007 | |
| WO | 2007055355 | A1 | | 5/2007 | |
| WO | WO2007053105 | A | * | 5/2007 | |
| WO | 2018220153 | A1 | | 12/2018 | |
| WO | WO-2018220153 | A1 | * | 12/2018 | ............. G01K 17/04 |
| WO | WO-2019086251 | A1 | * | 5/2019 | ............. B01L 3/505 |

OTHER PUBLICATIONS

Written Opinion of the International Searching Authority of PCT/EP2018/078475, dated Nov. 2, 2018 (12 pages).

* cited by examiner

CALORIMETER AND SAMPLE CONTAINER FOR A CALORIMETER

CROSS-REFERENCE TO RELATED APPLICATIONS

This application is a U.S. national stage filing under 35 U.S.C. 371 of international patent application no. PCT/EP2018/078475, filed on Oct. 18, 2018, which claims priority to European patent application no. EP17200227.1, filed on Nov. 6, 2017, the contents of both of which are incorporated herein by reference in their entirety.

TECHNICAL FIELD

The invention is directed to a calorimeter and a sample container for a calorimeter. Such a calorimeter can be used for the analysis of chemical or physiological processes which generate heat. Heat can be an indicator for a chemical reaction, a metabolic activity or a cellular function, e.g. a cellular function in micro-organisms, such as bacteria. In the most general sense, a calorimeter is a device measuring the heat produced by a sample inside a container being used as a recipient of such a sample. In an isothermal calorimeter, the heat generated by the sample is continuously removed while keeping the temperature difference between the interior of the container and the external heat sink minimal, ideally close to zero. The heat produced corresponds to a heat flux which can be measured by a sensor, such as a contact temperature sensor, e.g. a thermometer, a thermo-electrical sensor, a thermistor, a transistor, a resistance temperature detector (RTD), a platinum resistance thermometer, a thermo-mechanical sensor, or a non-contact sensor, such as an infrared optical sensor, a diode.

Biological processes can produce heat in the range of less than 1 microwatt per milliliter sample volume, which requires a high thermal sensitivity of the sensor used, thus involving microcalorimetry, in particular isothermal microcalorimetry allowing the detection of heat energies in the Nanowatt range. The heat flux to be detected can be in the range of 1 nanowatt up to and including 1000 microwatt. Preferably the heat flux can be in the range of 1 nanowatt up to and including 1 microwatt.

DESCRIPTION OF RELATED ART

A thermistor is a type of sensor which can be used in microcalorimetry. A thermistor is a thermally sensitive resistor. In particular a negative temperature coefficient thermistor (NTC) can be used, which is characterized in that the resistance of the thermistor is inversely proportional to the temperature sensed by the thermistor. Thermistors are characterized by a high gain, which enables them to resolve very small temperatures in a given temperature range.

A thermoelectric element is a device that converts a current into a heat flow or a heat flow into a current making use of thermoelectricity. Thermoelectricity describes the correlation between temperature and electricity. A thermoelectric element can be used for converting an electrical current into a heat flow, or a heat flow into a current. The conversion of a current into a heat flow is known as the Peltier effect, finding its application in a Peltier element. A Peltier element consists of two electrically conducting materials which are different from each other and which are connected to each other at one of each ends. The Peltier effect can be observed best if the electrically conducting materials are semiconductors. One of the electrically conducting materials is a p-type semiconductor, whereas the other electrically conducting material is a n-type semiconductor. An electric circuit including a battery can be connected to the free ends of the p-type semiconductor and the n-type semiconductor. If the electric circuit is closed, electrons from the negative pole of the battery flow into the direction of the p-type semiconductor and move along inside this p-semiconductor by filling up the positive "holes" in this material until they arrive at the boundary between the p-type semiconductor and the n-type semiconductor. Due to the fact, that in the n-type semiconductor, all available "holes" in the crystal structure have a negative polarity, the movement of the electrons is at least temporarily blocked by the boundary and requires energy to overcome this blockage. If the boundary is attached to a bridging heat exchange surface, such a bridging heat exchange surface cools as an energy input is required to deblock the electrons and "push" them through the n-type semiconductor to uphold the potential difference as applied by the electric circuit with the battery. On their way to the positive pole of the battery, the energy transported together with the electrons dissipates at the respective ends of the p-type semiconductor and the n-type semiconductor, whereby a heat flow is generated. If a heat exchange surface is provided at the source-sided ends of the p-type semiconductor and the n-type semiconductor, the temperature of this heat exchange surface rises, such that it becomes a hot surface.

If two different materials are connected at their ends together to form a loop whereby the contact surfaces of the two materials are brought to different temperatures, the thermoelectricity results in the generation of an electric circuit current. In case that the same arrangement of a p-type semiconductor and a n-type semiconductor is used, the heat supplied to the boundary connecting surface of the two semiconductors results in a thermodiffusion as the hot end of the p and n semiconductors contains more electrons of a higher energy which move towards the cold end and the cold end containing more electrons of a low energy moving to the hot end. This thermodiffusion results in a current difference also due to the use of different materials. In case the electrical circuit is interrupted, a potential difference results, which can be measured as a voltage, the Seebeck voltage. The Seebeck voltage is ideally roughly parallel to the temperature difference. A thermoelement can be used as a temperature sensor, provided it is calibrated accordingly.

A Peltier element can be used for the conversion of current into a heat flow. The inverse operation of a Peltier element results in a current generator, whereby by means of the Seebeck effect the heat flow can be converted into a current. If the electric circuit is interrupted this current results in a potential difference, which can be measured as a voltage. A thermoelement can be considered as a device generating an electromotive force and may be used as a sensor by measuring a voltage obtained from a current from a heat flow resulting from thermodiffusion.

A plurality of thermocouples can be combined to form a stack, a so-called thermopile. Such a thermopile is a multi-layer thermocouple, which can be used to measure a heat flow from a sample involving e.g. a biological process to a heat sink using a thermoelectric element as sensor.

The use of multi-channel calorimeters has been described in US 2004/0107986. Such a multi-channel calorimeter comprises a plurality of wells arranged in an array, whereby each of the wells is configured as a sample container. The sample container comprises a bottom surface, which is configured to receive a thermal sensor, such as a thermistor. The thermistor is received in a corresponding recess of the bottom surface. The bottom surface is configured to provide minimal resistance to heat flow, therefore the wall thickness of the bottom surface is reduced with respect of the other wall surfaces of the well which are not in contact with any thermal sensor. A plurality of wells can be arranged in a regular pattern on the well plate to allow for parallel measurements.

A drawback of the known calorimeter is to be seen in the fact that it is expensive to manufacture. In addition, the required measurement may take as long as a couple of days which makes it unsuitable for preliminary check-ups. A further disadvantage of the prior art calorimeter is that it uses a sample container which is in contact with a sensor arranged at the bottom end of the sample container. Such a sample container may have the shape of a bottle. The bottom of the bottle is in contact with the sensor whereas the bottle walls have to be thermally insulated to be able to detect the total heat flux generated by the sample. This results in a small heat exchange surface as most of the sample container cannot be used as heat exchange surface due to the configuration of the sensor used.

Calorimeters have also been designed for measuring the heat development of a continuous flow of medium, for instance the microcalorimeter of GB2093995 A. The flowable medium passes through a helical tube wound around a cylinder containing an ampoule. The helical tube is arranged in a helical groove of the cylinder. The tube passes below two thermodetectors containing Peltier elements arranged on the outer surface of the cylinder.

It has been contemplated in document WO2007053105 A1 to provide a biosensor which comprises a housing, a holder, a pair of heat sinks and a pair of heat reflectors which are thermally floating relative to the heat sinks suspended in the holder and thermally floating relative to the environment inside the holder and housing, thus a sample of biofluid flows continuously through the reaction chamber. The biosensor according to WO2007053105 A1 is therefore suitable to measure the heat generated in the sample in a floating temperature state. The sample container of WO2007053105 A1 is clamped in a retaining device which exerts a mechanical pressure onto the surface of the sample container by means of compressible o-rings.

The pair of heat sinks is thus configured to absorb any heat generated by the sample. A measurement process of less than 2 min is required to ensure, that all heat is absorbed by the heat sinks. For this reason, the biosensor according to WO2007053105 A1 is not suitable for measurements of a longer duration. This biosensor is therefore used to measure the heat generated by fast enzymatic reactions which are completed in less than 2 minutes. It is thus an object of the invention to provide a calorimeter configured such that the time required for completion of a measurement can be reduced for a thermally controlled environment. It is a further object of the invention to provide a calorimeter capable of completing the measurement within a time frame of at most 8 hours, preferably at most 4 hours, most preferably at most 2 hours. It is a further object of the invention to provide a calorimeter which can be used for a plurality of simultaneous measurements of a plurality of samples. It is a further object of the invention to provide a calorimeter which is simple in its manufacture and easy to assemble and to use.

The problem is solved by a calorimeter according to claim 1 and a sample container according to claim 7. Further advantageous embodiments of the calorimeter are subject to claims 2-6 and further advantageous embodiments of the sample container are subject to claims 8 to 15.

If the term «for instance» is used in the following description, the term relates to embodiments or examples, which is not to construed as a more preferred application of the teaching of the invention. The terms "preferably" or "preferred" are to be understood such that they relate to an example from a number of embodiments and/or examples which is not to construed as a more preferred application of the teaching of the invention. Accordingly, the terms "for example", "preferably" or "preferred" may relate to a plurality of embodiments and/or examples.

The subsequent detailed description contains different embodiments of the calorimeter and the sample container according to the invention. The calorimeter and the sample container can be manufactured in different sizes making use of different materials, such that the reference to a specific size or a specific material is to be considered as merely exemplary. In the description, the terms «contain», «comprise», «are configured as» in relation to any technical feature are thus to be understood that they contain the respective feature but are not limited to embodiments containing only this respective feature.

SUMMARY OF THE INVENTION

A system comprising a calorimeter for measuring a heat flux of a sample comprises a recipient space for a sample container containing a sample, a heat sink, a first heat transducer, whereby the first heat transducer comprises a first heat receiving surface in contact with the sample container when the sample container is positioned in the recipient space and a first heat absorbing surface in contact with the heat sink. A second heat transducer is provided, whereby the second heat transducer has a second heat receiving surface in contact with the heat sink and a second heat absorbing surface in contact with the sample container, when the sample container is positioned in the recipient space. The temperature in the recipient space is thereby controllable. The sample contained in the sample container is enclosed in the sample container when the measurement is performed. In particular, there occurs no sample flow through the sample container during the measurement period, i.e. for the duration of the measurement process. Thereby stationary conditions for the sample are obtainable in the sample container such that the heat generation in a stationary sample container and consequently also in the recipient space can be measured. According to an embodiment, the sample container is removable from the recipient space.

According to an embodiment, the measurement period has a duration of at least 10 minutes.

According to an embodiment, the measurement period has a duration of at least 30 minutes. According to any of the embodiments, the duration measurement period is not limited. The assembly of the first and second heat transducers of the invention is such that the heat can pass from the heat receiving surface of the first transducer through the sample container containing the sample to the heat absorbing surface of the second transducer. Thereby a heat flow through the sample container containing the sample is obtainable instead of a sample flow as disclosed in document WO2007053105 A1. For this reason, the sample container is in contact at the same time with at least one of the heat receiving surfaces and at least one of the heat absorbing surfaces of the respective first and second heat transducers. By the arrangement of the first and second heat transducers, the heat exchange of the heat transducers with the environment is forced.

According to an embodiment the sample container is positioned in the recipient space by moving it into the recipient space in an upright position. The sample container can be manually held on its top section and thus hanging freely during such manipulation. The sample container is adaptable to the recipient space. Thus, the sample container can fit snugly into a recipient space of any shape, in particular an u-shaped or v-shaped recipient space. In particular, the sample container can adapt to the shape of the first and second heat transducers when brought in contact with them.

A directed heat flow can thereby be obtained through the first heat transducer, the sample container and the second heat transducer. The first and second heat transducers are in particular configured to generate an electromotive force equivalent to the heat flux to or from the respective heat sink to be sent to a detecting unit for obtaining an electrical potential representing the heat flux leaving or traversing the container as disclosed in co-pending patent application PCT/EP2018/064411.

According to an embodiment, an insulating member is provided to insulate the recipient space in any location other than the location of the first and second heat transducers, whereby the insulating member is in particular a thermal insulating member.

According to an embodiment, the recipient space is provided between the first and second heat transducers. Each of the first and second heat transducers can be configured as a plate-shaped element. The first and second heat transducers can form a portion of the side walls of the recipient space. In particular, the first and second heat transducers can be the portion of the side walls of the recipient space exposed to the first and second container walls of the sample container. The first and second heat transducers can be arranged in such a way that a v-shaped recipient space is obtained. By a v-shaped recipient space, it is intended, that the side walls forming the lateral boundaries of the recipient space are arranged in a v-shape when viewed in section. An advantage of the v-shaped recipient space is the possibility to position the sample container in the recipient space with greater ease. In other words, the requirements to the precision of the positioning of the sample are thus considerably reduced. Furthermore, the sample container is automatically centered in its position and it remains in this position due to the gravitational forces acting on the sample container. Thereby it is possible to use a sample container manipulation unit to place the sample container in the recipient space by an automatic or semiautomatic manipulation.

If the sample container is disposed with container walls of a variable contour, the contour of the container walls can adapt to the side walls of the recipient space, such that the container walls remain in contact with the side walls during the entire measurement period. In particular, if a container with flexible container walls is used, the flexible container walls rest on the side walls and remain thereby in contact with the side walls. A sample container including flexible container walls can for instance be configured as a pouch. If the sample container contains a liquid sample, the sample exerts a hydraulic pressure on the flexible container walls. Thereby the container walls are pressed against the side walls of the recipient space and any air gap between the container walls and the side walls of the recipient space is avoided. In particular, the portion of the side wall or the side walls which are formed by the first and second heat transducers is therefore in contact with the container walls so to provide a minimal barrier against the transfer of heat from the sample to the heat transducer.

Each of the first and second heat transducer elements can comprise a heat receiving surface and a heat absorbing surface for generating an electromotive force equivalent to the heat flux to or from the heat sink to be sent to a detecting unit for obtaining an electrical potential representing the heat flux from the container. The use of a first and second heat transducer has the advantage that a heat flux difference between the first and second transducer can be measured, if the first heat transducer is mounted in a flipped configuration with respect to the second heat transducer. One of the heat absorbing surfaces and one of the heat receiving surfaces can face the sample container or can be attached to the container wall or sample container walls or the sample container walls rest on one of the heat absorbing surfaces and one of the heat receiving surfaces. One of the heat absorbing surfaces and one of the heat receiving surfaces can face the heat sink. One of the heat absorbing surfaces and one of the heat receiving surfaces can be attached to or rest on the heat sink. If the heat absorbing and/or heat receiving surfaces are attached to the container wall or walls, heat is transferred to the heat receiving surfaces and/or heat absorbing surfaces predominantly through conduction. The heat transfer by conduction is particularly advantageous if a portion of the sample container walls attached to or resting on at least one of the heat absorbing or heat receiving surfaces corresponds to at least 40% of the container wall surface. More preferably the portion of the sample container wall attached to or resting on at least one of the heat absorbing or heat receiving surfaces corresponds to at least 50% of the container wall surface. Most preferred, the portion of the sample container attached to or resting on at least one of the heat absorbing or heat receiving surfaces corresponds to at least 60% of the container surface.

The same configuration would also work for an arrangement containing only a single heat transducer. However, in an arrangement containing only a single heat transducer, any currents which are induced by the Seebeck effect of the heat transducer would be contained in the measurement, for this reason an embodiment containing a first and second heat transducer is considered to be a particularly preferred embodiment.

Furthermore, the distance between the lower edges of the first and second heat transducers can be smaller than the thickness of the sample container. Thereby, it can be ensured that the sample container is positioned accurately between the first and second heat transducers. According to this embodiment, the recipient space is substantially provided between the first and second heat transducers.

Alternatively, the first and second heat transducers can be arranged in such a way that a u-shaped recipient space is obtained. A u-shaped recipient space is advantageous as the sample container can be placed into the recipient space with a particular good fit, whereby any losses due to insufficient direct contact between the heat transducers are avoided.

According to an embodiment, the recipient space extends between the first and second heat transducers arranged next to each other at the same side of the recipient space and the insulating member on the opposite side of the recipient space. The first and second heat transducers thus form only one of the first or second side walls of the recipient space. The other side wall is formed by the insulating member. Thereby, a heat flux is directed to one of the side walls, whereas no heat exchange or heat transfer occurs at the opposite side wall formed by an insulating member.

Each of first and second heat transducers can be provided with electrical connectors connected by electrical conduits to a detecting unit such that—if in operation—a current is generated by the heat flux, the current is directed to the detecting unit for detecting an electrical signal indicative of the heat flux sensed by the first and second heat transducers.

A sample container for a system according to any of the embodiments comprises a first container wall, a second container wall and a connecting element connecting the first container wall with the second container wall, whereby the first and second container walls, the connecting element, a bottom section and a top section form a sample space. The bottom section and the top section are connected to each other by the first and second container walls and the connecting element. An opening is provided in the top section, whereby the opening in the top section is connected to the sample space for placing a sample to the sample space. At least one of the first or second container walls has a variable contour. The container walls can adapt to the side walls of the recipient space, such that the container walls remain in contact with the side walls during the entire measurement period. In particular, at least one of the first and second container walls can be flexible. The sample space can be disposed between the container walls. The sample space can be disposed in particular in a pouch or a bag. The sample container can be configured as a flexible substantially flat pouch or bag. The sample container can be configured as a flexible, thin body pouch or bag. The sample container can be configured as a flexible plastic pouch or bag. According to an embodiment, the plastic comprises one of a thermoplastic polymer, an elastomer, a duroplastic polymer. The container walls of the sample container can include more than one layer, for instance can be configured as a composite foil. Each of the layers can comprise one of a polymer or a metal. The metal can for instance comprise an aluminum foil. The composite foil can be manufactured by a method from selected from the group of extrusion, lamination methods.

According to an embodiment, the distance D1 between the first and second container wall is less than a third of the smaller one of the distances D2 between the top section and the bottom section or D3 between the lateral sides of the container. The distance D1 between the first and second container wall corresponds to the thickness of the sample space including the thickness of the container walls. This distance is measured from the outer surface of the first container wall to the outer surface of the second container wall. If these outer surfaces are planar and substantially parallel to each other, the distance D1 is measured in a direction normally to the outer surfaces. If the outer surfaces are not parallel to each other, D1 corresponds to the maximal distance measured in a horizontal plane intersecting the sample space if the sample container is positioned in an upright position, that means that the opening forms the uppermost portion of the sample container.

The distance D2 between the top section and the bottom section of the container is measured in a vertical plane if the sample container is positioned in an upright position, that means that the opening forms the uppermost portion of the sample container. If the container is of a substantially rectangular shape, the distance between the top section and the bottom section corresponds to the distance extending in normal direction to the horizontal sides of the rectangle. According to an embodiment, the lower horizontal side can include the ends of the connecting element at the bottom, the upper horizontal side is the side which contains the lower end of the connecting conduit.

The distance D3 between the lateral sides of first and second container wall is measured in a horizontal plane, if the sample container is positioned in an upright position, that means that the opening forms the uppermost portion of the sample container. If the container is of a substantially rectangular shape, the distance D3 between the lateral sides corresponds to the distance extending in normal direction to the vertical sides of the rectangle.

If the container is of non-rectangular shape, the distance D2 corresponds to the maximum extension of the container in vertical direction excluding any connecting conduit. The distance D3 corresponds to the maximum extension of the container in horizontal direction.

Advantageously, the distance D1 and the distance D3 are not the same. Advantageously, each of the distances D2 or D3 is greater than the distance D1. Instead of distance D1, it can be referred to a first distance. Instead of distance D2, it can be referred to a second distance. Instead of distance D3, it can be referred to a third distance.

The distance D3 can be up to 100 mm. According to a preferred embodiment the distance D3 is about 80 mm.

The top section comprises a guiding element. According to an embodiment, the guiding element comprises a rib. According to an embodiment, the guiding element comprises a plurality of ribs. A connecting conduit can be provided to connect the opening to the sample space. The guiding element can extend in a direction substantially normal to the axis of the connecting conduit. Each of the ribs can have a thickness in the range of 0.5 mm up to and including 5 mm. The normal distance between two neighboring ribs is in the range of 5 mm to 50 mm. The ribs can have a length which is at minimum 2 mm greater than the diameter of the connecting conduit and correspond to the distance D3. The width of the ribs is advantageously greater than the distance D1.

The sample container according to any of the preceding embodiments can be used for a sample containing a heat source and a gas for a measurement of the generation of heat in the sample by at least one of a chemical reaction, cell activity, a biological metabolism, bacteria in the sample. The gas can be air.

The opening of the container can be closable by a closure cap. The closure cap can comprise an elastomer, which may provide a fluid-tight sealing even after being punched with a needle. The needle can be like the needle used with the Multi-Adapter of Sarstedt (Art. Nr 14.1205). The needle is used to punch the sealing of the opening for filling a sample and the appropriate amount of air or any other gas into the recipient space of the sample container. A closure cap can also include a screw closure or a lid clip. A closure cap can be provided with a tamper-evident safety seal. The closure cap can be closed after the sample has been filled into the sample space or the sample containment space of the sample container and the tamper-evident safety seal provides an indication to the investigator if the sample may have been manipulated after the sampling process.

An inner container can be provided in the sample space for applications, in which a defined sample containment space size is required. The sample containment space is the space inside the inner container. The sample containment space is configured to receive a sample. The sample can be supplied to the sample containment space by the medium exchange element. The sample containment space is advantageously smaller than the sample space.

The inner container can have a height dimension d2 and a length dimension d3. The length dimension d3 is according to an embodiment smaller than the third distance D3. The height dimension d2 is according to an embodiment smaller than the second distance D2. The connecting element can have a thickness T. According to an embodiment, the length dimension d3 is smaller than the difference of the third distance D3 minus two times the thickness T. The height dimension d2 is smaller than the difference of the second distance D2 minus the thickness T. In case that the thickness T is not constant, the above-mentioned condition applies to the largest value of the thickness T of the connecting element.

The length dimension d3 can according to an embodiment be at most 60 mm. In particular, the length dimension d3 can be 10 mm up to and including 60 mm. The height dimension d2 can according to an embodiment be at most 60 mm. In particular, the height dimension d2 can be 10 mm up to and including 60 mm.

If a sample is contained in the sample space, the sample space is arranged such, that its center of gravity is arranged at a fixed distance from the guiding element. If a sample is contained in the sample containment space, the sample containment space is arranged such, that its center of gravity is arranged at a fixed distance from the guiding element. In operation, the guiding element can be received in a guide rail. The guide rail can be arranged on the calorimeter or can be a portion of a sample container supply system, which can be temporarily attached to the calorimeter for providing a sample container to the calorimeter or discharging a sample container from the calorimeter.

According to an embodiment, the guide rail can extend in horizontal direction. The sample container can be supplied to the recipient space extending between the first heat transducer and the second heat transducer by moving it along the guide rail in a horizontal direction. For this reason, the distance between the guide rail and consequently the guiding element moving along the guide rail and the center of gravity of the sample containment space is fixed. Thereby the center of gravity of the sample containment space can be placed in a precisely defined position, such that the measurement conditions are always the same and consequently the measurement results are comparable.

The size of the sample space of the sample container and/or the size of the sample containment space of the inner container arranged inside the sample container can be standardized. If a sample container of standardized size can be used, the sample analysis procedure to be conducted by the calorimeter can be automatized to a large extent.

The system can include a plurality of calorimeters according to one of the embodiments. The calorimeters can be arrangement parallel to each other so to form a stack of calorimeters. Each of the calorimeters of the stack is configured to perform a heat flux of a sample. According to an embodiment the stack of calorimeters can be configured such, that the calorimeters are arranged on a common horizontal plane. The pedestal of the heat sink thus stands on a horizontal plane.

The recipient space of the calorimeter is advantageously open on the top. According to this embodiment, the sample container can be supplied to the recipient space in a vertical direction.

According to an embodiment the recipient space of the calorimeter is open on at least one lateral side. According to this embodiment, the sample container can be supplied to the recipient space in a horizontal direction. In addition thereto the recipient space can be open on the top. This configuration allows the supply of the sample container in a horizontal direction. In operation a sample can be supplied to the recipient space according to an embodiment by moving the sample container containing the sample along a horizontal guide rail. The horizontal guide rail can be a part of a sample container manipulation unit.

If a stack of calorimeters is provided, a plurality of sample containers can be supplied to the corresponding recipient spaces at the same time. Thereby a plurality of heat flux measurements can be performed at the same time. Even more a plurality of stacks of calorimeters can be stacked on top of each other to form a multi-storey stack. Each of the storeys can be disposed with corresponding guide rails, such that an array of sample containers can be supplied to the multi-storey stack of calorimeters.

A system of multi-storey stack calorimeters can be advantageously employed to perform a rapid screening of a large number of samples. The manipulation of the sample containers is simplified such that an array of sample containers can be supplied to the corresponding recipient spaces at the same time, thus in parallel. Thereby, multiple parallel measurements can be made at the same time which can be of interest if a large-scale screening of a large number of samples is to be performed.

BRIEF DESCRIPTION OF THE DRAWINGS

A number of exemplary embodiments of the calorimeter and the sample container are shown in the subsequent drawings.

DETAILED DESCRIPTION

Figure 1:
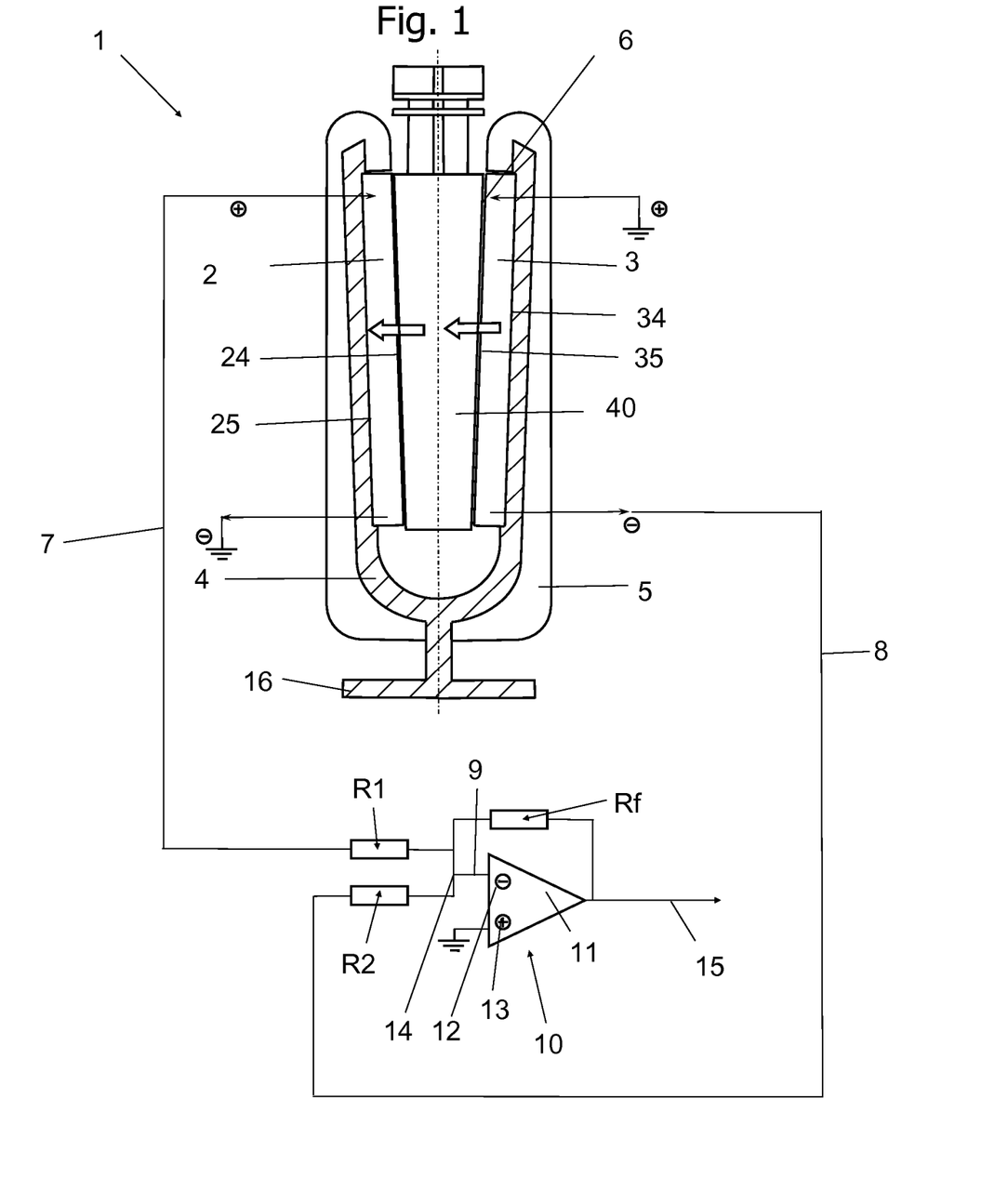
FIG. 1 shows a partially sectional view of a calorimeter according to a first embodiment of the invention, FIG. 2 a partially sectional view of a calorimeter according to a second embodiment of the invention, FIG. 3 a front view of a sample container according to a first embodiment of the invention, FIG. 4 a side view of the sample container of FIG. 3, FIG. 5 a side view of the sample container of according to a second embodiment of the invention, FIG. 6 a detail of a heat transducer, FIG. 7 a partially sectional view of a calorimeter according to a third embodiment of the invention, FIG. 8 a side view of the sample container of according to a third embodiment of the invention, FIG. 9 a section through a sample container according to a first variant, FIG. 10 a section through a sample container according to a second variant.

FIG. 1 is a schematic partially sectional view of a calorimeter 1, in particular the portion of the calorimeter 1 which contains a sample. The sample is contained in a sample container 40. The sample is not visible as the sample container is not shown in section in FIG. 1. The calorimeter 1 for measuring a heat flux of the sample comprises a recipient space 6 for a sample container 40 containing the sample, a heat sink 4, a first heat transducer 2, whereby the first heat transducer 2 comprises a heat receiving surface 24 in contact with the sample container 40 when the sample container 40 is positioned in the recipient space 6 and a heat absorbing surface 25 in contact with the heat sink 4. A second heat transducer 3 is provided, whereby the second heat transducer 3 has a second heat receiving surface 34 in contact with the heat sink 4 and a second heat absorbing surface 35 in contact with the sample container 40, when the sample container 40 is positioned in the recipient space 6. The heat sink 4 can comprise a pedestal 16.

The sample container 40 is removable from the recipient space 6. The first heat transducer 2 can be a plate-shaped element. The second heat transducer 3 can also be a plate-shaped element. The first heat transducer 3 and the second heat transducer 3 form the portion of the side walls of the recipient space 6 exposed to the first and second container walls 41, 42 of the sample container 40. The first and second heat transducers 2, 3 can be arranged in such a way that a v-shaped recipient space 6 is obtained. A v-shaped recipient space is advantageous as the sample container 40 can be placed into the recipient space 6 easily, also by making use of a sample container manipulation unit, whereby an automatic or semiautomatic manipulation of the sample container 40 can be realized. Furthermore, the distance between the lower edges of the first and second heat transducers 2, 3 can be smaller than the thickness of the sample container 40. Thereby it is ensured that the sample container 40 is positioned accurately between the first and second heat transducers 2, 3. According to this embodiment, the recipient space 6 is provided between the first and second heat transducers 2, 3. According to this embodiment the recipient space 6 is open to the top and to at least one lateral side. The top is according to this arrangement opposite to the pedestal 16. The bottom surface of the pedestal 16 can be arranged in a horizontal plane.

According to an embodiment, an insulating member 5 is provided to insulate the recipient space 6 in any location other than the location of the first and second heat transducers 2, 3. The insulating member 5 is in particular a thermal insulating member. The insulating member ensures that the entire heat flux is directed to the first and second heat transducers 2, 3, whereby it can be guaranteed that the entire heat flux is measured by the first and second heat transducers 2, 3.

Figure 6:
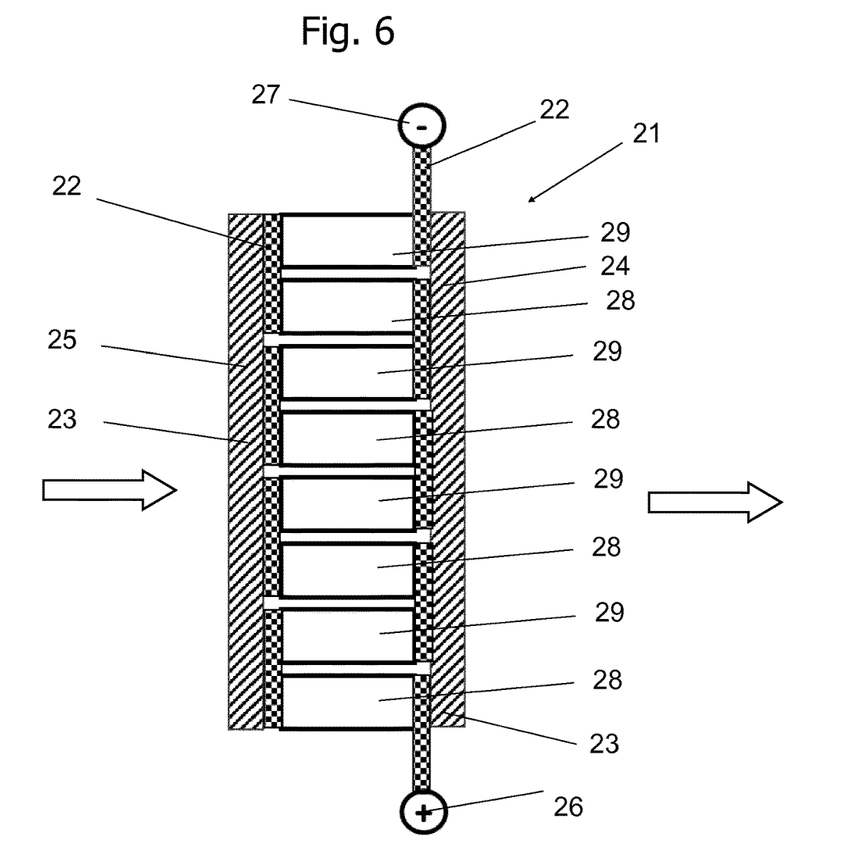

Each of first and second heat transducers 2, 3 are provided with electrical connectors 22 as shown in FIG. 6 connected by electrical conduits 7, 8 to a detecting unit 10 such that in operation a current is generated by the heat flux, the current is directed to the detecting unit 10 for detecting an electrical signal indicative of the heat flux sensed by the first and second heat transducers 2,3.

The detecting unit 10 comprises a first electrical conduit 7 connecting the detecting unit 10 with the first heat transducer 2. A resistor R1 is arranged in the first conduit to provide a current output which is directed to summing point 14. The detecting unit 10 comprises a second electrical conduit 8 connecting the detecting unit 10 with the second heat transducer 3. A resistor R2 is arranged in the second conduit to provide a current output which is directed to summing point 14. A third electrical conduit 9 leads from the summing point 14 to the negative input 12 of an amplifier 11. The positive input of amplifier 11 is connected to earth.

The combined output current from summing point 14 is introduced through the third electrical conduit 9 into the amplifier 11 via the negative input 12. Due to the fact, that the current in the first electrical conduit 7 leaving resistor R1 has the opposite direction compared to the current in the second electrical conduit 8 leaving resistor R2, the difference of these two currents is obtained in the summing point 14. The resulting current may be zero Amperes, if the current from R1 and the current from R2 have the same absolute value. The ohmic resistance of each of resistors R1 or R2 could be zero ohms, whereby the non-zero Seebeck currents are canceled out. Therefore, the antiparallel mounting of the first and second heat transducers 2, 3 of the calorimeter 1 results in an elimination of the non-zero Seebeck currents which have to be dealt with by any calorimeter according to the prior art. The resistor Rf is used in the amplification process.

The summing amplifier 11 generates an output voltage 15 which corresponds to the heat flux generated in sample container 40. The summing amplifier 11 comprises a positive input 13, which is connected to earth. The use of the summing amplifier 11 makes it possible to reliably detect very small heat flows, such as those emitted any type of chemical reaction or biological process, e.g. by cell activity, pathogens or bacteria. The heat flux can be registered for a certain time period and may be characteristic to a certain phenomenon. Therefore, the location of the peaks in the heat flux curve can be used to detect the species of pathogens, cells or bacteria present in the sample in the container 40. Therefore, the calorimeter 1 is not only useful to detect the presence of a heat source in the sample, it can be also useful also to determine the type of heat source, e.g. the species of pathogens, cells or bacteria responsible for the heat generation.

Figure 2:
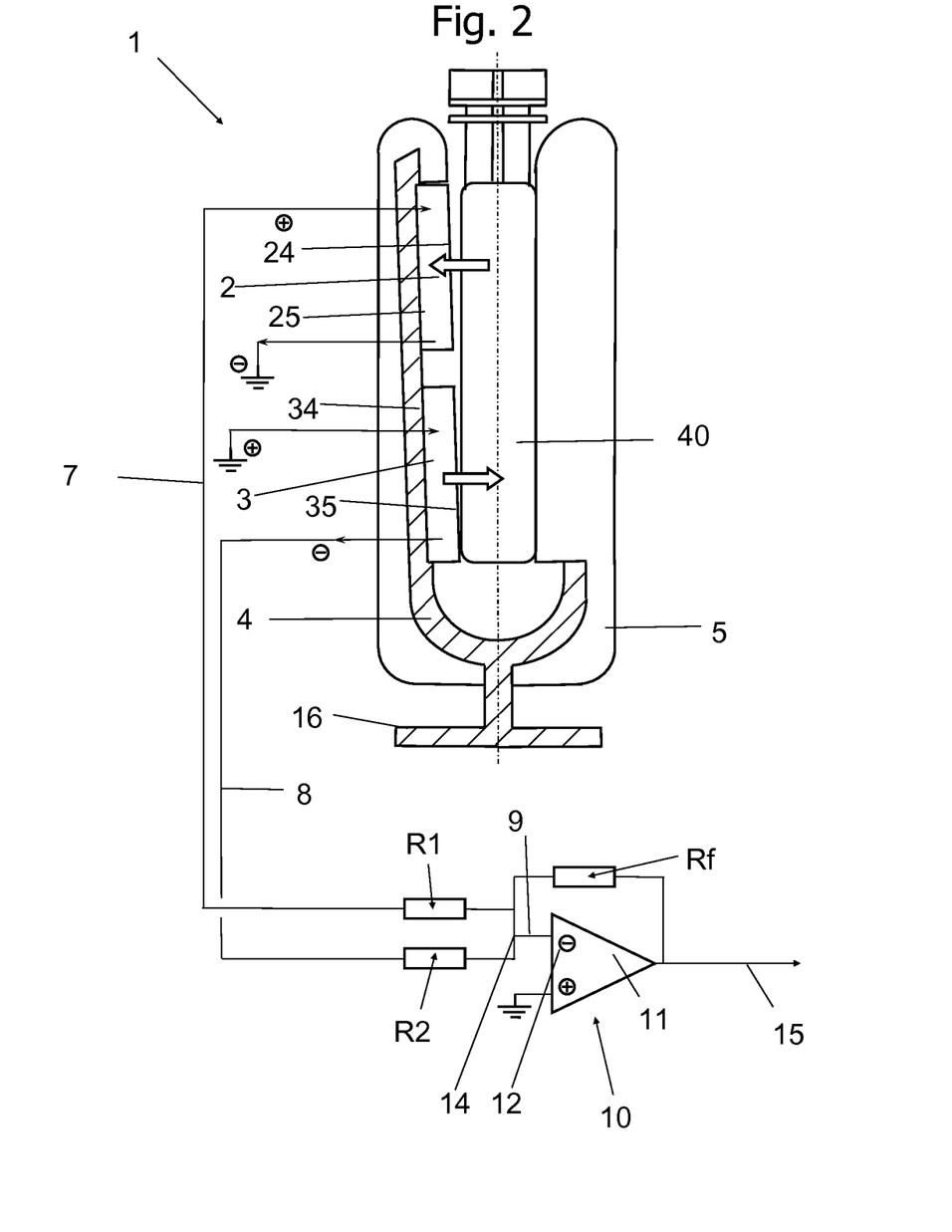

FIG. 2 shows a calorimeter of a configuration which differs from the configuration shown in FIG. 1. The reference numbers of FIG. 1 have been used also for this embodiment for the parts which are the same or have the same function. According to the embodiment shown in FIG. 2, the recipient space 6 extends between the first and second heat transducers 2, 3 arranged next to each other at the same side of the recipient space 6 and the insulating member 5 on the opposite side of the recipient space 6. The first heat transducer 2 can be a plate-shaped element. The second heat transducer 3 can also be a plate-shaped element. The first heat transducer 3 and the second heat transducer 3 form the portion of one of the side walls of the recipient space 6 exposed to the first container wall 41. Alternatively, the first and second heat transducers 2, 3 face the container wall 42. The first and second heat transducers 2, 3 can be arranged in such a way that a v-shaped recipient space 6 is obtained. A v-shaped recipient space is advantageous as the sample container 40 can be placed into the recipient space 6 easily, also by making use of a configuration which is not shown in the drawings as it is substantially a mirror shaped arrangement of the embodiment according to FIG. 2. The sample container 40 comprises a manipulation unit, whereby an automatic or semiautomatic manipulation of the sample container 40 can be achieved. Furthermore, the distance between the lower edges of the first and second heat transducers 2, 3 forming one side wall of the recipient space 6 and the insulating member 5 arranged on the opposite side and forming the other side wall of the recipient space 6 can be smaller than the thickness of the sample container 40. Thereby it is ensured, that the sample container 40 is positioned accurately between the first and second transducers 2, 3.

Figure 3:
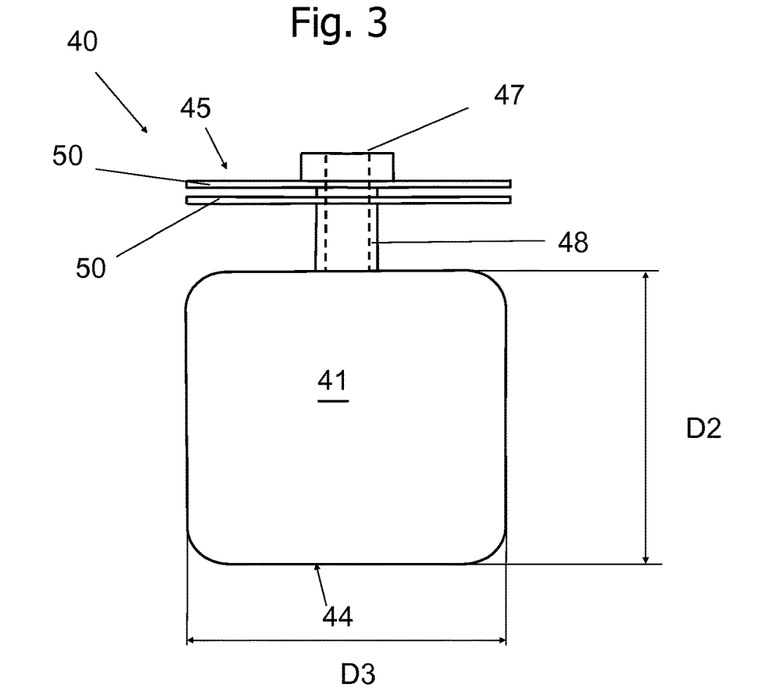
Figure 4:
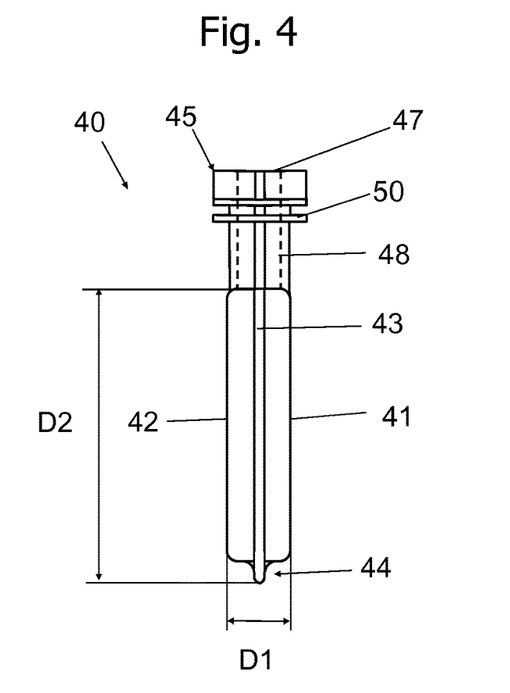
Figure 9:
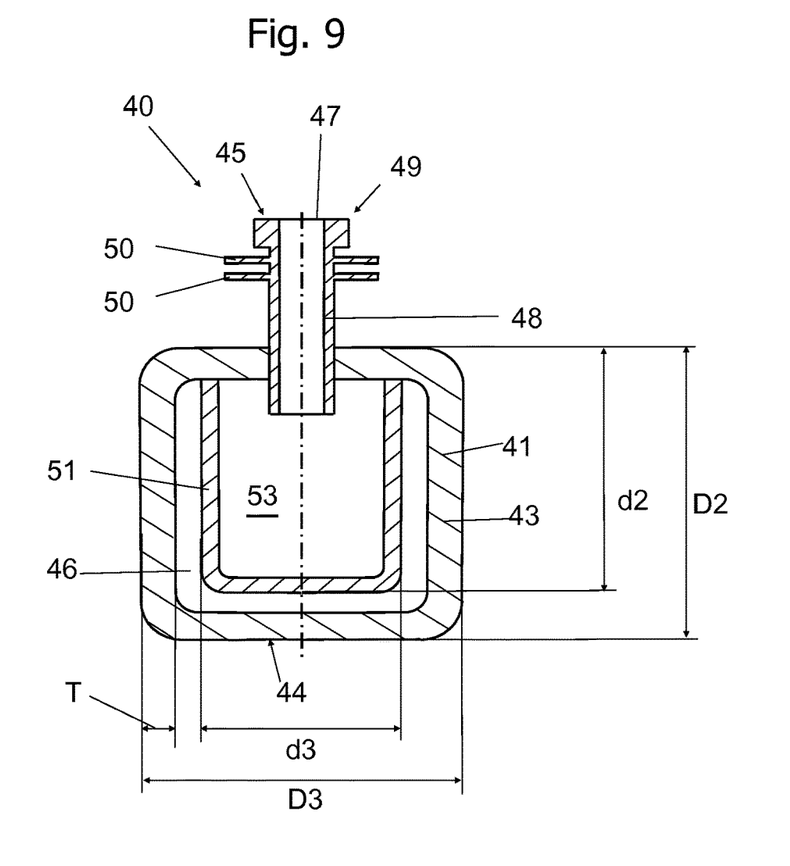

FIG. 3 and FIG. 4 show a sample container 40 for a calorimeter 1 according to any of the preceding embodiments. The sample container 40 comprises a first container wall 41, a second container wall 42 and a connecting element 43 connecting the first container wall 41 with the second container wall 42 whereby the first container wall 41, the second container wall 42, the connecting element 43, a bottom section 44 and a top section 45 to form a sample space 46. The sample space 46 is not visible in FIG. 3 or FIG. 4. FIG. 9 shows a section of a sample container 40 which shows the interior of the sample container and consequently a configuration of the sample space 46. The connecting element 43 can be shaped as a protruding portion such as a seam or a rib. The bottom section 44 and the top section 45 are connected to each other by the first and second container walls 41, 42 and the connecting element 43. An opening 47 is provided in particular at the top end of the top section 45. The opening 47 in the top section 45 is connected to the sample space 46 for placing a sample into the sample space 46. At least one of the first or second container walls 41, 42 is disposed with a variable contour.

In particular, at least one of the first and second container walls 41, 42 is flexible. The wall thickness of the first and second container walls is advantageously less than 1 mm if manufactured by an injection molding process. The wall thickness of the first and second container walls can be 50 micrometers up to and including 200 micrometers if a foil is used. The sample space 46 can be disposed inside a bag, whereby the bag can be a flexible bag, in particular a flexible plastic bag. The container 40 can be configured as a bag in particular a flexible bag.

The distance between the first and second container wall 41, 42 according to the embodiment of FIG. 3 or 4 corresponds to less than a third of the distance between the top section 45 and the bottom section 44. The distance between the first and second container walls 41, 42 corresponds to the wall thickness of the sample container 40. The wall thickness can be variable if the sample container 40 is configured as a flexible bag. In particular, the wall thickness of the empty sample container 40 can be less than the wall thickness of the container when a sample is contained in the container 40.

The top section 45 can comprise a guiding element 50. The guiding element 50 can be used by a sample container placement unit not shown in the drawings to place the sample container 40 into the recipient space 6 of a calorimeter 1 according to any of the embodiments of FIG. 1, FIG. 2 or FIG. 7. The guiding element 50 can comprise a plurality of ribs. The configuration of FIG. 1-4 shows two ribs arranged parallel to each other. The two parallel ribs allow for an exact positioning of the sample container in the recipient space 6.

A connecting conduit 48 is provided to connect the opening 47 to the sample space 46. The guiding element 50 extends in a direction substantially normal to the axis of the connecting conduit 48.

Figure 5:
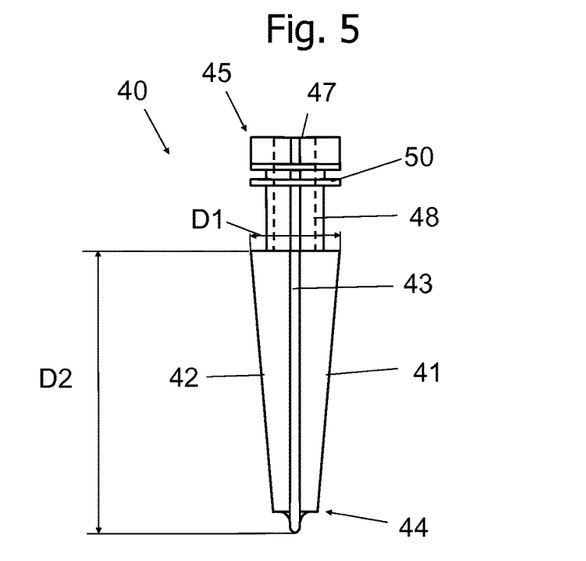

FIG. 5 shows a side view of a further embodiment of a sample container 40. The sample container 40 according to FIG. 5 differs from the sample container 40 of FIGS. 3 and 4 in that the first container wall 41 and the second container wall 42 are not substantially parallel to each other but are arranged in a V-shape. Advantageously the V-shape of the first and second container walls 41, 42 corresponds to the V-shape of the recipient space 6. The first and second container walls 41, 42 can fit exactly into the recipient space 6. The first and second container walls 41, 42 can be made of rigid material as the heat transfer between the first and/or second container walls 41, 42 and the first and second heat transducers 2, 3 can be optimized as the container walls 41, 42 are in direct contact with the first and second heat transducers 2, 3.

FIG. 6 shows an example of a heat transducer element 21 which can be the same as the first and second heat transducer elements 2,3 used in the previous embodiments. The heat transducer element thereby operates as a heat-flow sensor. The heat transducer element is an electromotive force (emf) producing element being disposed with an internal resistor R. It transforms the heat-flow into electric power (voltage and/or current). The internal resistor is disposed with a temperature dependent resistance. The heat transducer element 21 comprises a heat receiving surface 24 and a heat absorbing surface 25. The heat receiving surface 24 and the heat absorbing surface can be in contact with a wall of the container or with a heat sink such as the heat sinks of any of FIG. 2-5.

The heat receiving surface 24 and the heat absorbing surface 25 comprise a thermally conductive electric insulator 23. A stack of layers including a conductive p material, and layers including a conductive n-material is arranged between the heat absorbing surface 25 and the heat receiving surface 24 so as to transform the heat flux from the heat absorbing surface 25 to the heat receiving surface 24 into an electric current. The layer including a conductive p material and the layer including a conductive n-material are advantageously arranged in an alternate arrangement in a stack, thus a layer including a conductive p material is followed by a layer including a conductive n-material and vice versa. The layer including a conductive p material 28 and the layer including a conductive n material 29 are connected by electric connectors 22 in such a way that the layer including a conductive p material 28 is always connected to a layer including a conductive n material 29 and a layer including a conductive n material 29 is always connected to a layer including a conductive p material 28. The two outermost conductors 22 are connected to end connectors 26, 27 leading to an electrical conduit. When operated as a sensor an applied heat-flux from the heat absorbing surface 25 to the heat receiving surface 24, the heat absorbing surface 25 is heated and the heat receiving surface 24 is cold, thereby a negative current is generated. When operated as a Peltier element, an applied positive current generates a heat-flow from heat absorbing surface 25 to heat receiving surface 24, thereby it cools the heat absorbing surface 25.

According to a further embodiment the heat transducer element can be configured as a thermistor. The thermistor may include a semiconductor material, e.g. a metallic oxide of manganese, nickel, cobalt, copper, uranium, iron, zinc, titanium, barium, magnesium. The temperature coefficient is determined by the properties of oxides in the mixture. The thermistor comprises a bead or rod and the first and second electrically conductive surfaces may be configured as electrical leads, in particular bifilar leads including an electrically conductive material, such as copper.

The sample container 40 according to any one of the previous embodiments can be used for a sample containing a heat source, the sample being used for a measurement of the generation of heat by at least one of a chemical reaction, cell activity, a biological metabolism, bacteria in the sample.

Figure 7:
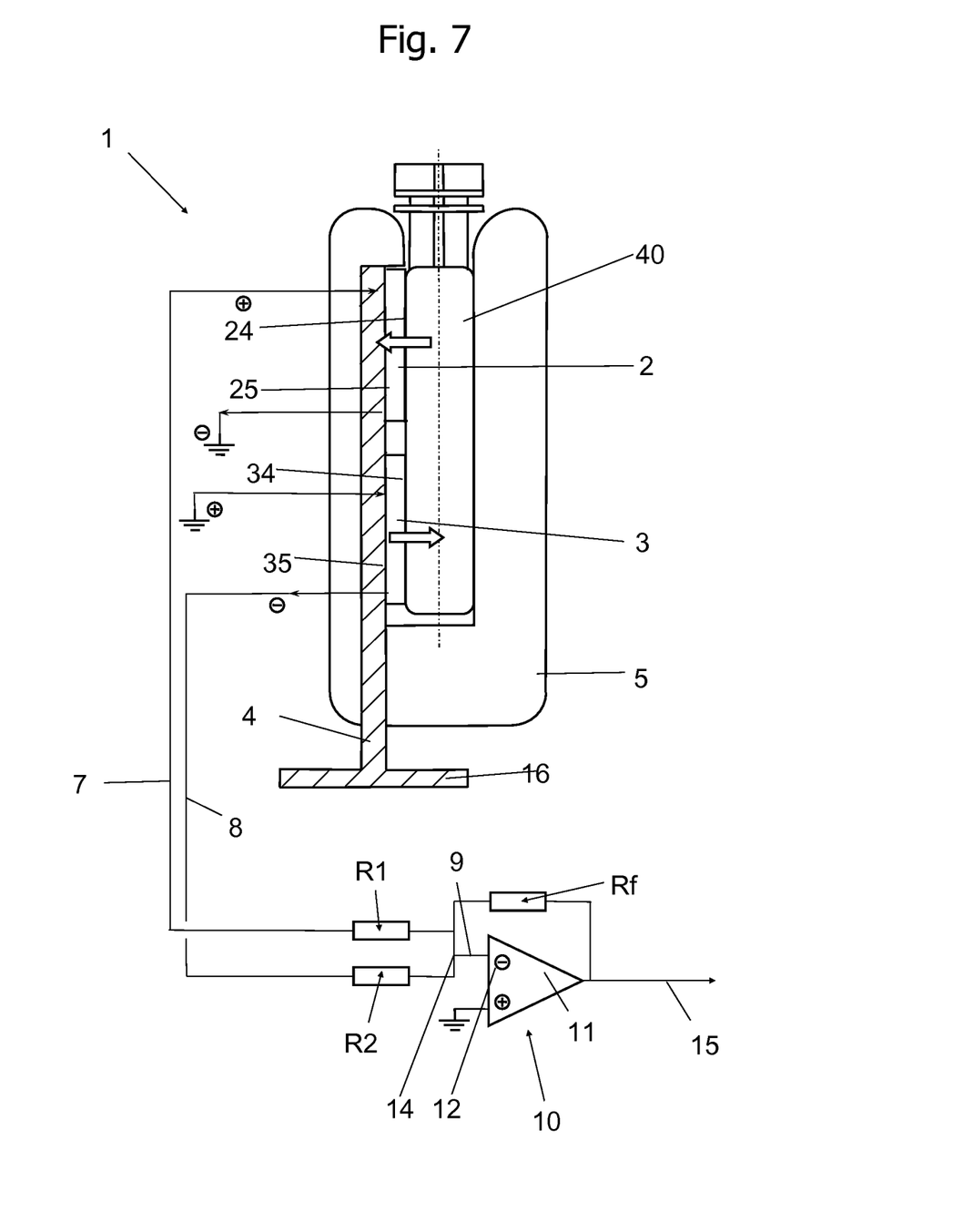

FIG. 7 shows a calorimeter 1 of a configuration which differs from the configuration shown in FIG. 1 or FIG. 2. The reference numbers of FIG. 1 have been used also for this embodiment for the parts which are the same or have the same function. According to the embodiment shown in FIG. 7, the recipient space 6 extends between the first and second heat transducers 2, 3 arranged next to each other at the same side of the recipient space 6 and the insulating member 5 on the opposite side of the recipient space 6. The recipient space 6 of the embodiment of FIG. 7 has parallel side walls. According to this embodiment, one of the side walls is essentially composed of the first and second heat transducers 3, 2 attached to the heat sink 4. The first heat transducer 2 can be a plate-shaped element. The second heat transducer 3 can also be a plate shaped element. The first heat transducer 2 and the second heat transducer 3 form the portion of one of the side walls of the recipient space 6 exposed to the first container wall 41. Alternatively, the first and second heat transducers 2, 3 face the container wall 42. The first and second heat transducers 2, 3 can be arranged in such a way that a u-shaped recipient space 6 is obtained. A u-shaped recipient space is advantageous as the sample container 40 can be placed into the recipient space 6 with a particular good fit, whereby any losses due to insufficient direct contact between the heat transducers 2, 3 are avoided. The sample container 40 comprises a manipulation unit, whereby an automatic or semiautomatic manipulation of the sample container 40 can be achieved. Furthermore, the distance between the lower edges of the first and second heat transducers 2, 3 forming one side wall of the recipient space 6 and the insulating member 5 arranged on the opposite side and forming the other side wall of the recipient space 6 substantially corresponds to the thickness of the sample container 40. Thereby it is ensured, that the sample container 40 is positioned accurately between the first and second transducers 2, 3. The speed and accuracy of the positioning of the sample container 40 in the recipient space can be further increased if the sample container 40 has a variable contour, whereby such a variable contour is obtained for instance if the first and second container walls 41, 42 are flexible.

Figure 8:
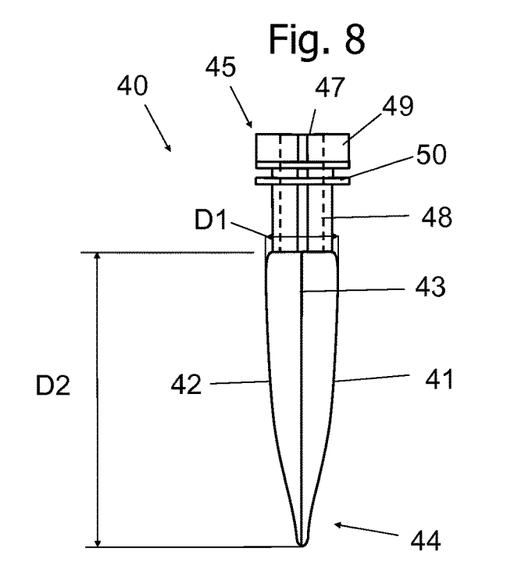

FIG. 8 is a variant of FIG. 5 and shows a side view of a further embodiment of a sample container 40. The sample container 40 according to FIG. 8 differs from the sample container 40 of FIG. 3, 4 or 5 in that the first container wall 41 and the second container wall 42 can be substantially parallel to each other, however may in particular in the state in which the sample container 40 contains a sample substantially deviate from a parallel configuration of the first and second container walls. At least in the filled state, that means that a sample is present in the sample container 40, the first container wall 41 is not parallel to the second container wall. Advantageously, the first and second container walls 41, 42 are flexible, thus they can change their shape to match the shape of the recipient space 6. The first and second container walls 41, 42 can thereby fit exactly into the recipient space 6. The first and second container walls 41, 42 can be made of flexible material. The flexible material can contain at least a layer of heat conducting material. The heat transfer between the first and/or second container walls 41, 42 and the first and second heat transducers 2, 3 can be optimized as the container walls 41, 42 are in direct contact with the first and second heat transducers 2, 3.

The top section 45 contains a medium exchange element 49. The medium exchange element 49 may comprise one of a filler or dispenser element. The medium exchange element contains an opening 47 for supplying or discharging a fluid or flowable sample into or from the container 40. The opening 47 is connected to the interior space of the container 40 bounded by the first and second container walls by a connecting conduit 48. The medium exchange element 49 can include a closure cap as for example shown in FIG. 10.

FIG. 9 shows a section through a sample container 40 according to a first variant. The sample container 40 includes a medium exchange element 49 which forms the top section 45 of the sample container 40. The medium exchange element 49 contains an opening 47 leading to the connecting conduit 48 for the supply or discharge of a sample to or from a sample space 46, which is provided between the first and second container walls 41, 42 as shown in one the previous embodiments. The second container wall 42 is not shown in this section as it lies in front of the section plane. The first container wall 41 is circumferentially connected to the second container wall 42 by a connecting element 43. The connecting element 43 can include one of a glue, a layer, a seam or it can also comprise a welding line. The first and second container walls are also attached to the medium exchange element 49. According to an embodiment, the connecting element 43 can also provide the connection between the first and second container walls 41, 42 and the medium exchange element 49. According to an embodiment a connection between the first and second container walls can be provided by thermal welding.

An inner container 51 can be provided in the sample space 46 for applications, in which a defined sample containment space 53 size is required. The sample containment space is the space inside the inner container 51. The sample containment space 53 is configured to receive a sample. The sample can be supplied to the sample containment space 53 by the medium exchange element 49. The sample containment space 53 is advantageously smaller than the sample space 46.

Figure 10:
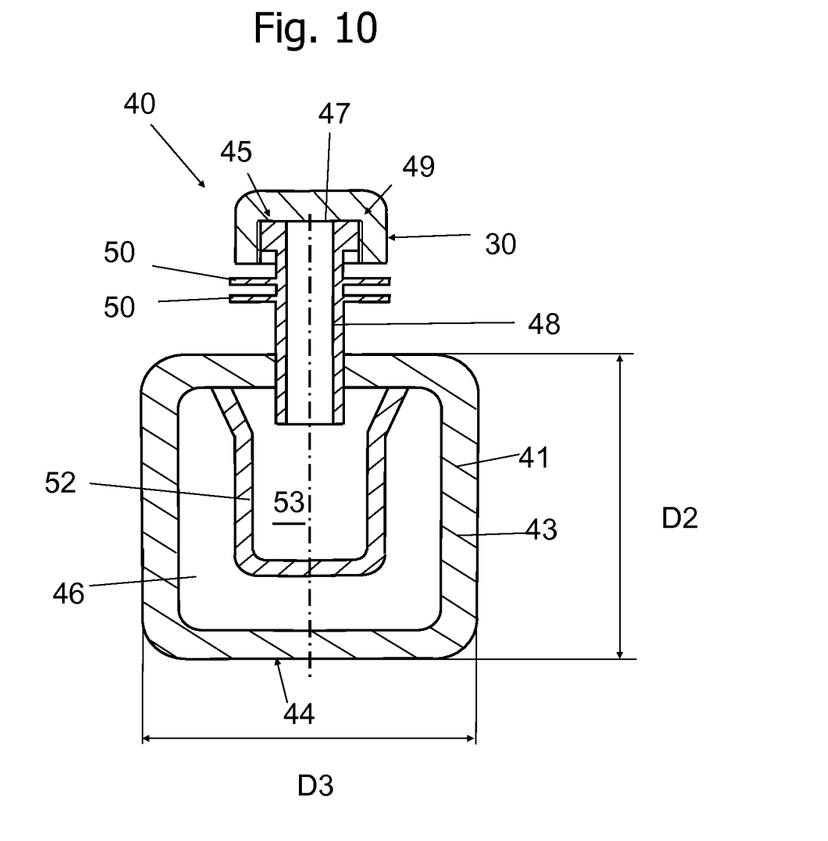

FIG. 10 shows a section through a sample container 40 according to a second variant, in which an inner container 52 of a smaller size and/or a different shape is provided. The sample container according to FIG. 10 has the same external dimensions as the sample container according to FIG. 9. If the dimensions of the sample container can be standardized, the manipulation of the sample containers can be automatized.

FIG. 10 also shows an example of a closure cap 30. A closure cap can include one of a screw closure or a lid clip. The closure cap 30 or the medium exchange element 49 can be provided with a tamper-evident safety seal. The closure cap can be closed after the sample has been filled into the sample space 46 or the sample containment space of the sample container 40. Any tamper-evident safety seal can provide an indication to the investigator if the sample may have been manipulated after completion of the sampling process.

The sample container 40 according to any of the preceding embodiments can be subject to a sterilization, for example an electron beam sterilization, in particular a gamma ray sterilization.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of an element or compound selected from the group consisting of A, B, C . . . and N, the text should be interpreted as requiring only one element from the group, not A plus N, or B plus N, etc.

The invention claimed is:

1. A system comprising a calorimeter for measuring a heat flux of a sample the calorimeter comprising a recipient space, a sample container containing a sample, a heat sink, a first heat transducer, wherein the first heat transducer comprises a first heat receiving surface in contact with the sample container in response to the sample container being positioned in the recipient space and a first heat absorbing surface in contact with the heat sink, wherein a second heat transducer is provided, wherein the second heat transducer has a second heat receiving surface in contact with the heat sink and a second heat absorbing surface in contact with the sample container, in response to the sample container being positioned in the recipient space, wherein an insulating member is provided to insulate the recipient space in any location other than the location of the first and second heat transducers and wherein the insulating member is a thermal insulating member.

2. The system of claim 1, wherein the sample container is removable from the recipient space.

3. The system of claim 1, wherein the recipient space is provided between the first and second heat transducers.

4. The system of claim 1, wherein the recipient space extends from the first to the second heat transducers arranged next to each other at a same side of the recipient space and the insulating member is arranged on an opposite side of the recipient space.

5. The system of claim 1, wherein each of first and second heat transducers is provided with electrical connectors connected by electrical conduits to a detecting unit such that if in operation a current is generated by the heat flux, the current is directed to the detecting unit for detecting an electrical signal indicative of the heat flux sensed by the first and second heat transducers.

6. A sample container for a system, comprising a calorimeter for measuring a heat flux of a sample, the calorimeter comprising a recipient space for receiving the sample container containing the sample, a heat sink, a first heat transducer, wherein the first heat transducer comprises a first heat receiving surface in contact with the sample container in response to the sample container being positioned in the recipient space and a first heat absorbing surface in contact with the heat sink, wherein a second heat transducer is provided, wherein the second heat transducer has a second heat receiving surface in contact with the heat sink and a second heat absorbing surface in contact with the sample container, in response to the sample container being positioned in the recipient space, wherein the sample container comprises a first container wall, a second container wall and a connecting element connecting the first container wall with the second container wall, wherein the first and second container walls, the connecting element, a bottom section and a top section form a sample space for placing a sample in the sample space, wherein the bottom section and the top section are connected to each other by the first and second container walls and the connecting element, wherein an opening is provided in the top section, wherein the opening in the top section is connected to the sample space, wherein the contour of at least one of the first or second container walls is configured to adapt to the side walls of the recipient space, such that the container walls remain in contact with the side walls during a measurement period.

7. The sample container of claim 6, wherein at least one of the first and second container walls is flexible.

8. The sample container of claim 6, wherein an inner container is provided in the sample space.

9. The sample container of claim 6, wherein the distance between the first container wall and the second container wall is less than a third of the distance between the top section and the bottom section.

10. The sample container of claim 6, wherein the top section comprises a guiding element.

11. The sample container of claim 10, wherein the guiding element comprises a plurality of ribs.

12. The sample container of claim 6, wherein a connecting conduit is provided to connect the opening to the sample space.

13. The sample container of claim 12, wherein a guiding element extends in a direction substantially normal to an axis of the connecting conduit.

14. The sample container of claim 6 for a sample containing a heat source and a gas for a measurement of the generation of heat in the sample by at least one of a chemical reaction, cell activity, a biological metabolism, bacteria in the sample.

15. A method for measuring a heat flux of a sample, comprising a calorimeter for measuring a heat flux of a sample, the calorimeter comprising a recipient space for receiving the sample container containing a sample, a heat sink, a first heat transducer, wherein the first heat transducer comprises a first heat receiving surface in contact with the sample container in response to the sample container being positioned in the recipient space and a first heat absorbing surface in contact with the heat sink, wherein a second heat transducer is provided, wherein the second heat transducer has a second heat receiving surface in contact with the heat sink and a second heat absorbing surface in contact with the sample container, in response to the sample container being positioned in the recipient space, wherein the sample container comprises a first container wall, a second container wall and a connecting element connecting the first container wall with the second container wall, wherein the first and second container walls, the connecting element, a bottom section and a top section form a sample space when the sample is placed in the sample space, wherein the bottom section and the top section are connected to each other by the first and second container walls and the connecting element, wherein an opening is provided in the top section, wherein the opening in the top section is connected to the sample space, wherein the contour of at least one of the first or second container walls adapts to the side walls of the recipient space, such that the container walls remain in contact with the side walls during a measurement period.

16. The method of claim 15, wherein the heat flux is generated in the sample by at least one of a chemical reaction, a cell activity, a biological metabolism, or bacteria present in the sample.

* * * * *